(12) United States Patent
Davies

(10) Patent No.: US 7,527,023 B2
(45) Date of Patent: May 5, 2009

(54) ANIMAL INSTRUMENTATION

(75) Inventor: Michael Allan Martin Davies, Concord, MA (US)

(73) Assignee: Equusys Incorporated, Sudbury, MA (US)

( * ) Notice: Subject to any disclaimer, the term of this patent is extended or adjusted under 35 U.S.C. 154(b) by 0 days.

(21) Appl. No.: 11/746,901

(22) Filed: May 10, 2007

(65) Prior Publication Data

US 2007/0204802 A1    Sep. 6, 2007

Related U.S. Application Data

(62) Division of application No. 11/136,201, filed on May 24, 2005.

(60) Provisional application No. 60/573,863, filed on May 24, 2004.

(51) Int. Cl.
*A01K 29/00* (2006.01)

(52) U.S. Cl. .................................................. 119/712

(58) Field of Classification Search ................. 119/712, 119/174, 840, 421; 340/573.3; 600/301
See application file for complete search history.

(56) References Cited

U.S. PATENT DOCUMENTS

| | | |
|---|---|---|
| 3,999,611 A | 12/1976 | Bucalo |
| 4,195,643 A | 4/1980 | Pratt, Jr. |
| 4,218,584 A | 8/1980 | Attenburrow |
| 4,233,845 A * | 11/1980 | Pratt, Jr. .................. 73/865.4 |
| 4,478,225 A | 10/1984 | Ewing |
| 4,540,001 A | 9/1985 | Ewing |
| 4,630,613 A | 12/1986 | Dennis |
| 4,703,217 A | 10/1987 | Ratzlaff et al. |
| 4,774,679 A | 9/1988 | Carlin |
| 4,935,887 A | 6/1990 | Abdalah et al. |
| 4,972,177 A | 11/1990 | Nolan |
| 5,081,991 A * | 1/1992 | Chance ..................... 600/411 |
| 5,138,550 A | 8/1992 | Abraham et al. |

(Continued)

FOREIGN PATENT DOCUMENTS

DE         195 46 022         6/1997

(Continued)

OTHER PUBLICATIONS

Back et al., "How the horse moves: 1. Significance of graphical representations of equine forelimb kinematics", Equine Vet. J., 27(1):31-38 (1995).

(Continued)

*Primary Examiner*—Yvonne R. Abbott
(74) *Attorney, Agent, or Firm*—Occhiuti Rohlicek & Tsao LLP

(57) ABSTRACT

An approach to monitoring, evaluation, diagnosis, treatment or conditioning of animals such as horses does not require use of restrictive equipment such as treadmills or force plates and that can provide either or both of more or less immediate or continuous processing of data to perform the monitoring or diagnosis. One or more wireless sensors are attached to the animal, for example, to measure motion-related parameter associated with one or more parts of the animal. Sensor data is received from the sensors and processed to identify a characteristic of the motion of the animal, such as a quality of gait. The sensor data can also be used to avoid injury to the animal and/or the rider, and to verify the identity of an animal.

10 Claims, 3 Drawing Sheets

U.S. PATENT DOCUMENTS

| | | | |
|---|---|---|---|
| 5,186,062 A | 2/1993 | Roost | |
| 5,373,852 A | 12/1994 | Harrison et al. | |
| 5,458,122 A | 10/1995 | Hethuin | |
| 5,483,970 A | 1/1996 | Rosenberg | |
| 5,485,402 A | 1/1996 | Smith et al. | |
| 5,736,656 A | 4/1998 | Fullen et al. | |
| 5,779,631 A | 7/1998 | Chance | |
| 5,791,350 A | 8/1998 | Morton | |
| 5,794,625 A | 8/1998 | McCarley et al. | |
| 5,844,862 A | 12/1998 | Cocatre-Zilgien | |
| 5,853,005 A | 12/1998 | Scanlon | |
| 5,873,821 A | 2/1999 | Chance et al. | |
| 5,955,667 A | 9/1999 | Fyfe | |
| 6,018,705 A | 1/2000 | Gaudet et al. | |
| 6,038,935 A | 3/2000 | Fullen et al. | |
| 6,052,654 A | 4/2000 | Gaudet et al. | |
| 6,093,146 A | 7/2000 | Filangeri | |
| 6,113,539 A | 9/2000 | Ridenour | |
| 6,135,055 A * | 10/2000 | Pratt | 119/51.02 |
| 6,228,037 B1 | 5/2001 | Derksen | |
| 6,266,623 B1 | 7/2001 | Vock et al. | |
| 6,301,964 B1 | 10/2001 | Fyfe et al. | |
| 6,421,453 B1 | 7/2002 | Kanevsky et al. | |
| 6,436,038 B1 | 8/2002 | Engstrom | |
| 6,498,994 B2 | 12/2002 | Vock et al. | |
| 6,513,381 B2 | 2/2003 | Fyfe et al. | |
| 6,532,901 B2 | 3/2003 | Isley et al. | |
| 6,536,377 B2 | 3/2003 | Beaver | |
| 6,549,795 B1 | 4/2003 | Chance | |
| 6,569,092 B1 | 5/2003 | Guichon et al. | |
| 6,602,209 B2 | 8/2003 | Lambert et al. | |
| 6,611,789 B1 | 8/2003 | Darley | |
| 6,625,302 B2 * | 9/2003 | Kalscheur et al. | 382/110 |
| 6,644,976 B2 | 11/2003 | Kullok et al. | |
| 6,659,960 B2 | 12/2003 | Derksen et al. | |
| 6,699,207 B2 | 3/2004 | Tasch et al. | |
| 6,974,373 B2 * | 12/2005 | Kriesel | 452/157 |
| 7,039,220 B2 * | 5/2006 | Kriesel | 382/110 |
| 7,054,784 B2 | 5/2006 | Flentov et al. | |
| 7,214,128 B2 * | 5/2007 | Kriesel | 452/157 |
| 2002/0010390 A1 | 1/2002 | Guice et al. | |
| 2002/0028003 A1 | 3/2002 | Krebs et al. | |
| 2002/0037092 A1 | 3/2002 | Craig et al. | |
| 2002/0046713 A1 | 4/2002 | Otto | |
| 2002/0055691 A1 | 5/2002 | Tasch et al. | |
| 2002/0082486 A1 | 6/2002 | Lavery et al. | |
| 2002/0107649 A1 | 8/2002 | Takiguchi et al. | |
| 2002/0123699 A1 | 9/2002 | Lambert et al. | |
| 2002/0187480 A1 | 12/2002 | Brandon | |
| 2003/0068605 A1 | 4/2003 | Kullok et al. | |
| 2003/0135097 A1 | 7/2003 | Wiederhold et al. | |
| 2003/0139692 A1 | 7/2003 | Barrey et al. | |
| 2003/0212348 A1 | 11/2003 | Lambert | |
| 2005/0224009 A1* | 10/2005 | Seder | 119/174 |
| 2007/0056516 A1* | 3/2007 | Nordlund et al. | 119/14.01 |

FOREIGN PATENT DOCUMENTS

| | | |
|---|---|---|
| DE | 19546022 | 6/1997 |
| DE | 197 07 413 | 8/1998 |
| DE | 19707413 | 8/1998 |
| DE | 103 37 235 | 3/2005 |
| DE | 10337235 | 3/2005 |
| EP | 0549081 | 6/1993 |
| GB | 2410553 | 8/2005 |
| WO | WO03/055388 | 7/2003 |
| WO | WO2004/041086 | 5/2004 |

OTHER PUBLICATIONS

Back et al., "How the horse moves: 2. Significance of graphical representations of equine hind limb kinematics", Equine Vet. J., 27(1):39-45 (1995).

Barrey et al., "Analysis of the equine jumping technique by accelerometry", Equine Vet. J. Suppl., 23:45-49 (1997).

Barrey et al., "Stride Characteristics of Overground versus Treadmill Locomotion in the Saddle Horse", Acta Anat., 146:90-94 (1993).

Barrey et al., "Techinque D'Appel du Chevel de Saut D'obstacles", EquAthlon, 29:12-15 (1997).

Barrey, "Methods, Applications and Limitations of Gait Analysis in Horses", The Veterinary Journal, 157:7-22 (1999).

Bertone, A.L., "Gait Analysis for the Quantification of Lameness" in Diagnosis and Management of Lameness in the Horse. St. Louis: Saunders, 2003, pp. 222-225.

Buchner et al, "Head and trunk movement adaptations in horses with experimentally induced fore-or hindlimb lameness", Equine Vet. J., 28(1):71-76 (1996).

Buchner et al., "Bilateral Lameness in Horses: A Kinematic Study", The Veterinary Quarterly, 17(3):103-105 (1995).

Buchner et al., "Body centre of mass movement in the lame horse", Equine Vet. J. Suppl., 33:122-127 (2001).

Buchner et al., "Body Centre of Mass Movement in the Sound Horse", The Veterinary Journal, 160:225-234 (2000).

Buchner et al., "Limb movement adaptations in horses with experimentally induced fore- or hindlimb lameness", Equine Vet. J., 28(1):63-70 (1996).

Buchner, "The advance of clinical biomechanics", Equine Vet. J., 33(5):430-432 (2001).

Burn et al., "Impact during equine locomotion: Techniques for measurement and analysis", Equine Vet J Suppl.,(23):9-12 (1997).

Clayton et al., "Measurement Techniques for Gait Analysis", Equine Locomotion, pp. 55-76.

Clayton et al., "The forelimb in walking horses: 2. Net joint moments and joint powers", Equine Vet. J., 32(4):295-299 (2000).

Clayton et al., "The hindlimb in walking horses: 2. Net joint moments and joint powers", Equine Vet. J., 33(1):44-48 (2001).

Clayton, "Comparison of the stride kinematics of the collected, medium, and extended walks in horses", Am. J. Vet. Res., 56(7):849-852 (1995).

Clayton, "Gait Analysis Comes of Age", The Veterinary Journal, 157:5-6 (1999).

Clayton, "Instrumentation and Techniques in Locomotion and Lameness", Veterinary Clinics of North America: Equine Practice, 12(2):337-350 (1996).

Clayton et al., "Assessment of the reliability of a technique to measure postural sway in horses", Am. J. Vet. Res., 64(11):1354-1359 (2003).

Colborne et al., "Joint moments and power in equine gait: a preliminary study", Equine Vet. Suppl., 23:33-36 (1997).

Colborne et al., "Power flow in the equine forelimb", Equine Vet. J. Suppl., 23:37-40 (1997).

DeLuzio et al., "A Procedure to Validate Three-Dimensional Motion Assessment Systems", J. Biomechanics, 26(6):753-759 (1993).

Drevemo et al., Equine locomotion: 1. The analysis of linear and temporal stride characteristics of trotting Standardbreds, Equine Vet. J., 12(2):60-65 (1980).

Drevemo et al., "Equine locomotion: 2. The analysis of coordination between limbs of trotting Standardbreds", Equine Vet. J., 12(2):66-70 (1980).

Drevemo et al., "Equine locomotion: 3. The reproducibility of gait in Standardbred trotters", Equine Vet. J., 12(2):71-73 (1980).

Dutto et al., "Moments and power generated by the horse (Equus Caballus) hind limb during jumping", The Journal of Experimental Biology, 207:667-674 (2004).

Dyson, Sue J., "Poor Performance and Lameness" in Diagnosis and Management of Lameness in the Horse. St. Louis: Saunders, 2003, pp. 828-832.

Equimetrix (downloaded from www.equimetrix.com on Mar. 18, 2004).

Downloaded from www.equineptech.com Dec. 14, 2004.
Faber et al., "Three-dimensional kinematics of the equine spine during canter", Equine Vet. J., 33:145-149 (2001).
Fingerman, Dan, "Static Measurements and Moving Targets: Privacy, Biometrics and the Consumer-Bank Relationship", Jan. 2003.
Fredricson et al., "The application of high-speed cinematography for the quantitative analysis of equine locomotion", Equine Vet. J., 12(2):54-59 (1980).
Fredricson et al., "Treadmill for equine locomotion analysis", Equine Vet. J., 15(2):111-115 (1983).
Hodson et al., "The forelimb in walking horses: 1. Kinematics and ground reaction forces", Equine Vet. J., 32(4):287-294 (2000).
Hodson et al., "The hindlimb in walking horses: 1. Kinematics and ground reaction forces", Equine Vet. J., 33(1):38-43 (2001).
Hoyt, "Time of Contact and Step Length: The Effect of Limb Length, Running Speed, Load Carrying and Incline", *The Journal of Experimental Biology*, 203, (2000), pp. 221-220.
Judy et al., "Evaluation of an in-shoe pressure measurement system in horses", Am. J. Vet. R., 62(1):23-28 (2001).
Keegan et al., "A curve-fitting technique for evaluating head movement to measure forelimb lameness in horses", Biomedical Sciences Instrumentation, 36:239-244 (2000).
Keegan et al., "Accelerometer-Based System for the Detection of Lameness in Horses", Biomed Sci Instrum., 38:107-112 (2002).
Keegan et al., "Changes in kinematic variables observed during pressure-induced forelimb lameness in adult horses trotting on a treadmill", Am. J. Vet. Res., 61(6):612-619 (2000).
Keegan et al., "Detection of lameness and determination of the affected forelimb in horses by use of continuous wavelet transformation and neural network classification of kinematic data", Am. J. Vet. Res., 64(11):1376-1381 (2003).
Keegan et al., "Effects of anesthesia of the palmar digital nerves on kinematic gait analysis in horses with and without navicular diseases", Am. J. Vet. Res., 58(3):218-223 (1997).
Keegan et al., "Effects of Balancing and Shoeing of the Forelimb Feet on Kinematic Gait Analysis in Five Horses with Navicular Disease". Retrieved from the Internet: <URL: http://www.neosoft.com/~iaep/pages/protected/jissues/j1808/j1808p522.html.
Keegan et al., "Evaluation of a sensor-based system of motion analysis for detection and quantification of forelimb and hind limb lameness in horses", Am. J. Vet. Res., 65(5):665-670 (2004).
Keegan et al., "Evaluation of mild lameness in horses trotting on a treadmill by clinicians and interns or residents and correlation of their assessments with kinematic gait analysis", Am. J. Vet. Res., 59(11):1370-1377 (1998).
Keegan et al., "Signal decomposition method of evaluating head movement to measure induced forelimb lameness in horses trotting on a treadmill", Equine Vet. J., 33(5):446-451 (2001).
Kramer et al., "Kinematics of the hind limb in trotting horses after induced lameness of the distal intertarsal and tarsometatarsal joints and intra-articular administration of anesthetic", Am. J. Vet. Res., 61(9):1031-1036 (2000).
Kramer et al., "Objective determination of pelvic movement during hind limb lameness by use of a signal decomposition method and pelvic height differences", Am. J. Vet. Res., 65(6):741-747 (2004).
Leach et al., "Standardised terminology for the description and analysis of equine locomotion", Equine. Vet. J., 16(6):522-528 (1984).
Leach et al., "Stride Characteristics of Horses Competing in Grand Prix Jumping", Am. J. Vet. Res., 45(5):888-892 (1984).

Leleu et al., "Analysis of trotter gait on the track by accelerometry and image analysis", Equine Vet. J. Suppl., 34:344-348 (2002).
Les Haras Nationaux, Comite D'Orientation Scientifique et Technique "Compte redu des recherches soutenues par les Haras nationaux en 2002" Oct. 2003, No. 10, 4 pages.
Linford, "Camera speeds for optoelectronic assessment of stride-timing characteristics in horses at the trot", Am. J Vet. Res., 55(9):1189-1195 (1994).
Locometrix Press Release, Nov. 2003.
Martin, et al., "Experiences Using a High-Speed Treadmill to Evaluate Lameness" in Diagnosis and Management of Lameness in the Horse. St. Louis: Saunders, 2003, pp. 832-835.
Mayagoitia et al., "Accelerometer and rate gyroscope measurement of kinematics: an inexpensive alternative to optical motion analysis systems", Journal of Biomechanics, 35:537-542 (2002).
Pratt Jr. et al., "A Relationship Between Gait and Breakdown in the Horse", Am. J. Vet. Res., 39(2):249-253 (1978).
Roepstorff et al., "Concept of a Force-Measuring Horseshoe", Acta Anat., 146:114-119 (1993).
Savelberg et al., "Assessment of the horizontal, fore-aft component of the ground reaction force from insole pressure patterns by using artificial neural networks, aft component of the ground reaction force from insole pressure patterns by using artificial neural networks", Clinical Biomechanics, 14:585-592 (1999).
Savelberg et al., "Ground reaction forces in horses, assessed from hoof wall deformation using artificial neural networks", Equine Vet. J. Suppl., 23:6-8 (1997).
Schamhardt et al., "Measurement Techniques in Animal Locomotion Analysis", Acta Anat., 146:123-129 (1993).
Schamhardt et al., "Software for Analysis of Equine Ground Reaction Force Data", Computer Methods and Programs in Biomedicine, 23:247-253 (1986).
Schamhardt, "The Mechanics of Quadrupedal Locomotion. 'How is the Body Propelled by Muscles?'", Eur. J. Morphol., 36(4-5):272-279 (1998).
Sloet Van Oldruitenborgh-Oosterbaan et al., "Advantages and disadvantages of track vs. treadmill tests", Equine Vet. J. Suppl., 30:645-647 (1999).
Stashak, "Examination for Lameness", Adams' Lameness in Horses, Fifth Edition, (2002) Lippincott Williams & Wilkins pp. 113-121; 181-183.
Van den Bogert et al., "Multi-Body Modelling and Simulation of Animal Locomotion", Acta Anat., 146:95-102 (1993).
Van Den Bogert et al., "Simulation of Quadrupedal Locomotion Using a Rigid Body Model", J. Biomechanics, 22(1):33-41 (1989).
Van Wessum et al., "Electromyography in the Horse in Veterinary Medicine and in Veterinary Research—A Review", Veterinary Quarterly, 21(1):3-7 (1999).
Vorstenbosch et al., "Modeling study of compensatory head movements in lame horses", Am. J. Vet. Res., 58(7):713-718 (1997).
Weishaupt et al., "Assessment of gait irregularities in the horse: eye vs. gait analysis", Equine Vet. J. Suppl., 33:135-140 (2001).
Wilson et al., "General Biomechanics", Abstracts/Comparative Biochemistry and Physiology Part A, 132:S71-S80 (2002).
Winter, "Camera speeds for normal and pathological gait analyses", Med. & Biol. Eng. & Comput., 20:408-412 (1982).
International Preliminary Report on Patentability, PCT/US2005/018022, Dec. 7, 2006.
International Search Report and Written Opinion, PCT/US2005/018022, Dec. 2, 2005.

* cited by examiner

ANIMAL INSTRUMENTATION

CROSS-REFERENCE TO RELATED APPLICATIONS

This application is a divisional of U.S. application Ser. No. 11/136,201, filed May 24, 2005, which claims the benefit of U.S. Provisional Application No. 60/573,863 filed on May 24, 2004, which is incorporated herein by reference. This application is also related to International Application No. PCT/US05/018022, also titled "Animal Instrumentation," filed on May 24, 2005.

BACKGROUND

This document relates to animal instrumentation.

Objective evaluation and diagnosis of animals is difficult for a variety of reasons. Most obviously, unlike humans, animals cannot easily communicate with a person who is evaluating, diagnosing, treating or training them. For example, a horse cannot communicate which limb or joint hurts or in what way it hurts or under what condition it hurts. Another difficulty, especially for large or fast animals such as horses, is that it is difficult to obtain objective and quantitative measurements of physical or physiological parameters on an animal, that are accurate, or reproducible, or reflect real-world conditions or are available in real-time. For example, it can be difficult and expensive to bring a horse into a facility with suitable measurement equipment to obtain accurate and reproducible measurements, and these do not represent real-world conditions and may not be available in real time. As a consequence, evaluation and diagnosis and treatment and conditioning are typically based on subjective and qualitative judgments of veterinarians, trainers or riders.

An important area of evaluation and diagnosis relates to lameness in horses. Competitive horses are valuable assets. Furthermore, they are physically fragile and are particularly susceptible to lameness. Experts estimate that at any one time at least 10% of all equine athletes are clearly lame or injured or out of condition in some way that prevents them attaining peak performance, and many more have subtle or chronic conditions that are difficult to detect or need monitoring.

Therefore, it is desirable to apply effective evaluation and diagnosis techniques to diagnose injury, to prevent injury, to enable the treatment of injury or to aid in recovery from injury in order to protect their value. In addition, it is desirable to improve the effectiveness of programs for training and conditioning. Once lameness is discovered, lengthy rehabilitation is often necessary. Significant effort and expense is expended on many competitive horses. Lameness temporarily or even permanently negates the benefit of such significant investment.

Detection and diagnosis of lameness in horses today is largely based on subjective and qualitative evaluation. Typical techniques involve observation to detect asymmetries in motion, gross evaluation of a stationary animal such as by palpitation of limbs, and use of anesthetic blocking of nerves to determine if lameness is alleviated, for example, by blocking pain from a particular joint. Note that in this last technique, although the horse may appear less lame, the underlying cause of lameness may in fact cause further damage to the horse during the evaluation.

Modern medical and veterinary techniques can involve some objective and quantitative monitoring of physical and physiological parameters. For example, monitoring of physiological parameters (for example, an EKG) during treadmill-based exercise is a well-established diagnostic technique for people. Treadmill-based techniques are also used for animals such as horses, with notably increased difficulty associated with the size of the animal and the limited means of communication with the animal. For example, a lengthy period of acclimatization and the use of tranquilizing drugs may be required.

In the veterinary domain, when objective measurements are sought, monitoring and diagnosis of accurate and reproducible physical and physiological parameters has generally included the use of treadmill-based techniques, video monitoring using optical markers to track limb position, or the use of force plates upon which a horse steps. These approaches do not necessarily reflect real-world conditions or support continuous monitoring.

Ambulatory monitoring has been attempted using a sensor for acceleration or recording heart rate and respiratory sounds for large animals, including horses. In general, these various objective measurements are either limited in the duration of the trial, or in the accuracy and reproducibility of the data, or performed for a limited set of parameters at a time, such as using a single two-axis accelerometer at 50 Hz for a few minutes, or a single sound sensor. In addition, they are typically very costly.

Other types of systems provide assistance for subjective evaluation, such as facilitating mark-up of video captured using commercially available consumer camcorders and using this assisted subjective data as the basis for analysis. These approaches have time resolution in the range of 50 Hz or 60 Hz (limited by the video frame rate) and a few centimeters in space (limited by video resolution), and generally lack of reproducibility because of the subjective assessment involved.

SUMMARY

In one aspect, in general, an approach to instrumentation and telemetry of physiological and physical parameters of an animal and its environment has particular application to horses. This approach improves the effectiveness of one or more of evaluation, diagnosis, care conditioning or monitoring of animals because it does not require use of restrictive equipment such as treadmills or force plates, and it can provide objective and quantitative data that is accurate and reproducible, and this data can be obtained under real-world conditions, for either or both of more or less real-time or continuous processing of data to perform the monitoring or diagnosis. That is, in such an approach objective and quantitative data can be collected under real-world conditions and this data can be processed and the information can be displayed in real-time.

In another aspect, in general, a method involves measuring a characteristic of the motion of an animal and transmitting and processing and storing this information. One or more sensors are attached to the animal. These sensors include a sensor for measuring a motion-related parameter associated with a limb or other part of the animal. Sensor data is received from the sensors and processed to identify a characteristic of the motion of the animal and this information can optionally be displayed.

In another aspect, in general, a method for avoiding injury to an animal makes use of a number of sensors. Sensor signals are processed to identify the actual or potential for the injury condition, and feedback is provided to avoid the injury.

In another aspect, in general, a method for monitoring the treatment and recovery of an animal is related to either or both of accelerating the treatment and recovery or increasing the likelihood of a successful outcome. This method may be used to avoid bringing an animal back into competition or work before it is ready, or alternatively prolonging treatment and recovery any longer than necessary.

In another aspect, in general, a method relates to monitoring and improving the conditioning, training or preparation of an animal. The conditioning or training may extend over a prolonged period, and the improvement may involve changes in the approach or methods adopted. For example, if a horse is being trained and conditioned for an event, the improvement may include selecting when and which event to enter or whether or not to participate, or whether or not to continue training or how to continue training. The preparation may also include the choice or application or configuration of equipment (for example shoeing a horse by a farrier, or choosing a particular configuration of tack).

In another aspect, in general, a method relates evaluating or monitoring the potential performance of an animal. For example, this method can include evaluating the potential of a young or untrained animal, and then updating the estimates of the potential performance over time as the animal matures and undergoes training. The evaluation of potential may combine data from sensors with other data, such as measurements of conformation.

In another aspect, in general, a method relates to evaluating or monitoring the performance of the people involved in training or conditioning an animal or performing in competition, and improving their performance. For example, this can provide feedback to and guidance for a show-jumping rider to improve their performance or feedback to and guidance for a jockey riding a racehorse.

In another aspect, in general, a system for monitoring an animal includes a sensor subsystem fixed to the animal, including at least one sensor for measuring a physical parameter associated with at least one limb or the animal. A computing subsystem is used for real-time processing of data provided by the sensor subsystem. A communication subsystem couples the sensor subsystem and the computing subsystem and is for passing sensor data from the sensor subsystem to the processing subsystem.

In another aspect, in general, a system for monitoring an animal includes a communication hub for attaching to an animal. The communication hub includes a receiver for accepting sensor data from sensors attached to the animal and a transmitter for providing data based on the accepted sensor data. The system also includes a set of sensors, each including a transmitter for providing sensor data to the hub. The communication hub is configurable for receiving sensor data from a selection of the set of sensors attached to the animal.

Aspects of the invention can include one or more of the following features.

Multiple sensors are attached to the animal, each sensor providing at least some of the sensor data. The sensors can each measure a motion-related parameter associated with a different limb or part of the animal. The sensors can each measure a different motion-related parameter associated with a single limb of the animal, such as the movement of different portions of the limb.

The sensors monitoring the physical or physiological parameters of the animal include any set of one or more of: an inertial sensor to measure linear or rotational position, motion or acceleration; a force, strain or pressure sensor; a muscle, nerve or connective tissue activity sensor; a respiration sensor; a cardiac sensor; a blood oxygen sensor; an audio sensor; a visual sensor, such as an endoscope; or a temperature sensor. The sensors are optionally removably attached to the animal.

In addition, the system can include additional sensors that monitor the environment, including time and location, and temperature, humidity and atmospheric pressure.

The sensor data can include normal speed or high speed, standard definition or high definition video monitoring and recording.

The sensor data from a number of different sensors can be synchronized, so that users can assess multiple parameters at the same time, with reference to a common timeline. The processing of the received sensor data is in a real time mode, or alternatively in a batch mode. The sensor data or analyses of the sensor data and related data can be displayed at any speed, from a static snapshot, through interval by interval, slow motion, real-speed and speeded up.

The sensor data is collected during a normal activity of the animal, for example, during regular exercise, training or an athletic event. The received sensor data can be processed during the normal activity.

Identifying the characteristic of the motion includes identifying a quality of gait of the animal. The quality of the gait can include a physical parameter of the gait, such as stride length and timing, the timing of stance and swing phases, the relative timing and magnitude of linear or angular motion of limbs or other parts of the animal, such as the head. The quality of gait can include a lameness exhibited in the gait of the animal.

Processing the received sensor data includes identifying an injury condition based on the received signals, such as an actual injury or a predisposition to an injury.

The sensor data or other information can be passed over a wireless network local to the animal, and the sensor data or other information can be also passed over a wireless link to a station or server remote from the animal. For example, sensors for motion can typically use a low power wireless link for the short distance from the sensor to the hub, and then a higher power link for the longer distance from the hub to the receiving station, or server while the horse is in motion.

The sensor module can also include a small amount of memory to act as a buffer for storage of data, before it is transmitted to the hub. The hub can include a large amount of memory, sufficient to store data for several hours or even days, to allow extended monitoring when it is not feasible or desirable to transmit data from the hub to a station or server.

The sensor data can be secured, for example through using encryption techniques. This ensures that it cannot be intercepted or tampered with.

The system can authenticate the data that is being provided on the basis of time, based upon an internal reference clock or an external reference clock. It can authenticate the data as being provided at a certain location on the basis of internal references, such as inertial measurements, or through an external reference such as the Global Position System.

The system can include a method for authenticating the identity of animal involved in providing the data. For example, it may recognize an identifier associated with the animal, such as a radio frequency ID device, or genetic information. Alternatively, it can authenticate identity by establishing a chain of verification in which a trusted party authenticates the identity of the animal at the outset, and information gathered from sensors is then used to verify the physical signature of the animal, from the pattern of physical or physiological information such as motion.

This can include capturing visual data, photos or video, at the same time as physical data, and associating the information, so that it can be verified that the photos or video were taken at the same time and in the same place, and that the timing of the events in photos or video matches the sensor measurements.

The system for the storage, processing and display of information can be configurable and modular. The design rules for the partitioning of functionality into modules, and the interfaces between the modules can be clear and stable, so that the development of each module can be distributed and take place independently. This may include users or third parties developing modules. This enables the system to be adapted to a wide range of diverse applications.

The system allows information to be linked with or associated with other relevant information from the evaluation, diagnosis, care, conditioning or monitoring. For example, this includes notes or records provided by users or others, such as other diagnostic measurements or images or records. This also supports pattern recognition, by enabling the detection of linkages between quantitative and objective data provided by this system and the associated conditions or outcomes.

The system can allow remote monitoring of data in real-time or batch mode, so that a user who is not present can conduct or contribute to evaluation, diagnosis, care and conditioning. As part of this, the system can enable observations at multiple locations to be synchronized or coordinated, so that users can look at the same information at the same time.

Aspects of the invention can include one or more of the following advantages.

By allowing instrumentation without use of restrictive equipment (such as a treadmill or a force plate) information that is more representative of real-life condition of the animal may be obtained. For example, information related to a horse's physiological condition or physical performance can be obtained during low-stress conditions or during a competitive equestrian event.

By allowing instrumentation without the need for further subsequent off-line or batch processing of the data, such as analysis of video signals, real-time monitoring of the data may provide immediate feedback, which can be used to more quickly detect conditions and to take appropriate action.

Another advantage of instrumentation without use of restrictive equipment relates to cost. Use of specialized facilities for large animals, such as large animal treadmills, high speed video equipment or force plates, can be costly both for use of those facilities and for transporting the animal to such a facility. Use of relatively inexpensive equipment that can be attached and removed easily from the animal can greatly reduce cost and make such instrumentation available to a larger population of animals.

The instrumentation approach can be non-invasive. In particular, detailed evaluation and diagnosis of lameness without necessitating use of nerve blocking anesthetics has the advantage that the horse does not risk further physical damage during the evaluation procedure. In a successful application of the nerve blocking approach, if the limb or joint causing pain to the horse is blocked then the horse appears not to be lame or less lame. But because the horse does not experience the discomfort, further physical damage can occur while the anesthetic is active through physical activity that the anaesthetized horse would have avoided.

Availability of either or both of objective or quantitative information about an animal provides additional methods of diagnosis and assessment of training, conditioning or rehabilitation programs over methods based on subjective or qualitative information. For example, rather than relying on subjective or on qualitative information, for example, obtained by viewing the animal, objective and quantitative measurements that are accurate and reproducible can be used to detect subtle conditions, which are not readily apparent either because the size of the change in motion or in the pattern of motion is small or because the condition only becomes apparent when the horse is moving faster, at trot, canter or gallop.

In addition, by storing historical data for an animal, comparisons can be made over time of trend data (that is longitudinal comparisons), for example to assess progress in a conditioning or rehabilitation program. Furthermore, comparisons can be made among different animals of population data (that is horizontal comparisons), for example, to compare different animals' capabilities or their progress with equivalent training or recovery programs.

Information about a population of animals over a period of time and associated information such as evaluations, diagnoses, care or conditioning regimes enable pattern recognition, such as through statistical analysis or inference. This can assist or accelerate some or all of evaluation or diagnosis, providing closed-loop care. This pattern recognition can be automated, so that the selection of algorithms and the analysis of information do not require further action or intervention. This pattern recognition and feedback can include providing feedback to someone evaluating, caring for or using the horse in real-time. The system can provide automatic pattern recognition with feedback in real-time, for example to provide a visual or audible alert to a rider of a lameness condition while riding the horse.

Use of wireless sensors, such as small lightweight wireless sensors, can improve ease of use through easy attachment and removal of sensors from an animal without requiring the attachment of wires to collect sensor data. Such wireless communication may provide less restriction on movement than wired approaches. In addition, the wireless approach may provide increased robustness and reliability by removing a point of failure of a wired link.

Sensor components and radio components are integrated in a robust package that can withstand environment and shock/pressure conditions. This package can vary the transmission rate to minimize power consumption. It can include automatic calibration to compensate for gain, rates, offsets or drifts. This automatic calibration can be based on measurements from a single sensor package, or on results from multiple sensor packages, or on results from multiple tests and multiple animals. The power for this package can come partially or completely by scavenging from the motion of the animal. For example, in a horse the power can come from piezeo-electric methods using vibration when the horseshoe impacts the ground, or electro-magnetic methods when the leg is in motion.

A communication hub on the animal, for example, attached to the saddle of a horse (for example, in a weight pocket) or carried by the rider, may provide a way of improving communication between sensors and a remote station. For example, rather than each sensor necessarily being able to transmit a wireless signal to the remote station, the hub can aggregate the data and then transmit it to the remote station. As an example, a hub may receive sensor data over relatively low-power short-range wireless links, and then transmit the aggregated data to a remote station using a wireless link that has relatively higher-power or longer range.

A configurable and modular system for instrumentation and telemetry can be adapted for a wide variety of types and combinations of sensors. Furthermore, an automatic configuration of the system (for example of a hub) can increase the ease with which an animal is instrumented by removing the requirement that a user configure the system. For example, depending on the sensors that are present, the system can configure itself to communicate with each of the available sensors. For example, depending on the sensors that are providing signals, the system can configure itself to process the provided signals. For example, different processing algorithms can be selected automatically depending on the sensors that are available.

This self-configuration approach can also provide robustness to loss of sensors in real-life situations. For example, a system may be configured to analyze gait based on multiple accelerometers on limbs of an animal. If one of the accelerometers becomes unavailable because it is damaged, or starts transmitting erroneous data because it has become dislodged, the system may be able to reconfigure itself to use the remaining sensors.

Security and authenticity of data collected from an animal provides a number of commercial advantages, for example, related to avoidance of fraud in the sale of animals. The secure data can be used for identification purposes, thereby reducing a possibility an imposter to an animal being sold. Furthermore, longer-term monitoring of physical and physiological parameters can provide advantages in insurance underwriting by being able to identify material conditions.

A configurable and modular system for processing, storage and display can be adapted for a wide variety of applications. Furthermore, an automatic configuration of the processing, storage and display system can increase the ease of evaluation, diagnosis or monitoring by removing the requirement that a user configure this system. For example, depending on the information that is available, the system can configure itself to use algorithms appropriate to the application, and to display the results in a format appropriate to the application.

Furthermore, a modular system for storage, processing or display that has clear and well-defined interfaces for processing modules and for display modules of the information allows the development and deployment of these modules to be widely distributed. Users and third parties can contribute significant innovations in processing or pattern recognition or visualization, appropriate for a wide range of diverse applications.

The ability to have both local and remote access enables the optimum combination of individuals to evaluate, diagnose, care or monitor an animal, depending on the animal and the application. For example, if an animal is at a location remote from the people who typically provide care, they can contribute in conjunction with someone who is present with the animal. For example, in another application a local provider of care can obtain support from another practitioner with specialist expertise relevant to the animal or application.

The linkage to other information supports a complete cycle of closed loop care, in which quantitative and objective data that is accurate and reproducible is used in conjunction with other information, such as subjective observations, other diagnostic measurements or images, and training or veterinary records relating of the animals' condition or the outcome of care or conditioning regimes.

Other features and advantages of the invention are apparent from the following description, and from the claims.

DESCRIPTION

Figure 1:
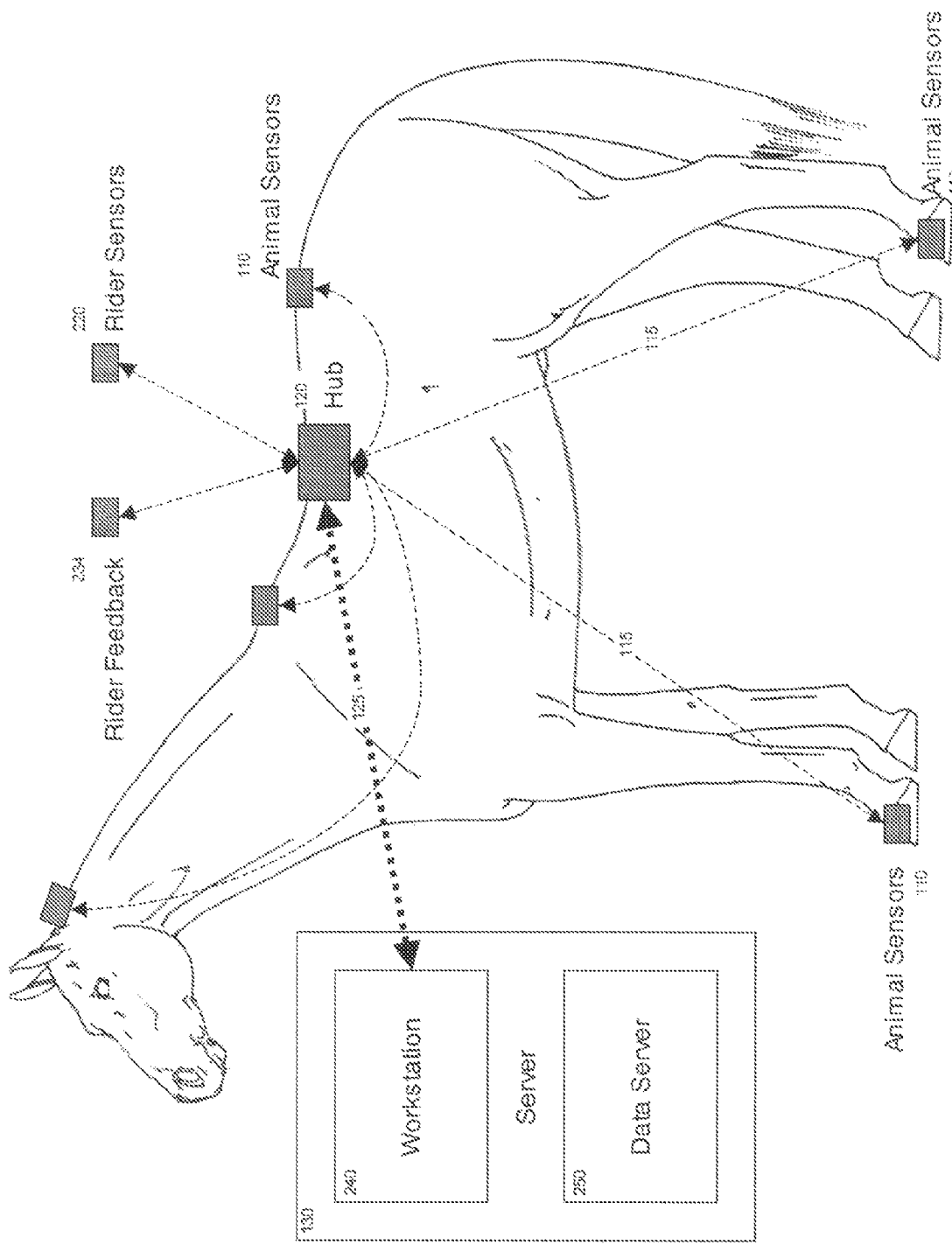
FIG. 1 is a schematic diagram of an equine instrumentation, telemetry and informatics system.

Referring to FIG. 1, an instrumentation and telemetry system 100 is used to collect and process information regarding physical and physiological parameters of a horse 101 and optionally of the horse's rider 102 and its environment. Before beginning monitoring or during the course of ongoing longer-term monitoring, a number of sensors 110 are attached to the horse. These sensors provide data to a hub 120, which is also attached to the horse or is alternatively carried by the rider 102 or located nearby, such as on a trailer. The hub provides some of the communication or processing or storage or display functionality for the system. Information from the sensors is received over communication links 115 at the hub 120, where it may be stored, and optionally transmitted immediately or subsequently over a communication link 125 to a remote server 130, which is typically stationary. Optionally, information is also transmitted to a display 122 or other audio, tactile or visual output device (for example a heads up eyeglass display, colored LEDs, or similar device) to provide feedback to the rider 102 of the horse.

The server 130 includes one or more workstations 240 for recording, processing and transmitting information generated from the sensor data, each of which has a user interface for report/display 244 and input/controls 246 (such as a terminal or a workstation with a display) through which a user can examine the information, and optionally one or more data servers 250, each of which stores animal data 252 and authentication data specifying access rights to this information. Computing resources for processing data from the sensors are hosted at the hub 120 and/or at the server 130. For example, the hub may host signal conditioning and, data reduction functions and data buffering, while the server may host information storage and analysis functions.

In a preferred mode of operation, the horse is not necessarily confined during the collection of data, although the system might be used in confined situations while still providing advantages over other systems. By not requiring that the horse be confined, the data can be collected during a normal activity. By normal activity, we mean activity that the horse would generally have undertaken had the collection of data not been desired or required. Such normal activities can range include, without limitation, roaming freely in a paddock, to routine exercise, to training for a competitive event (such as jumping or racing), to or actual competition.

A wide variety of sensors 110 can be used with the system in any particular monitoring situation. Some sensors relate to data collection for the analysis of gait, for example, to detect actual or propensity for lameness. Such sensors include inertial sensors that are attached to the limbs. Inertial sensors include linear and rotational accelerometers or gyroscopes. The information from such sensors is used for functions such as estimating limb positions or motion as a function of time or directly measuring asymmetric asymmetry of motion. Other sensors related to gait include strain, pressure or force sensors embedded in the horse shoes, sensors measuring joint movement or position, and physiological sensors that measure aspects such as nerve signals, muscle signals (electromyography), and muscle and tendon position or motion. As discussed further below, additional sensors, which are not necessarily directly related to gait analysis, can also be used.

In general, multiple sensors are used to generate concurrent recording, for example, from one or more of multiple limbs or from other parts of the horse such as the body, neck or head.

For example, one or more of inertial sensors or strain or pressure sensors attached to multiple legs of the horse as well as to the horse's head or neck provide data that can be combined to analyze the gait of the horse. In addition, multiple sensors can be used on one limb, for example to track the motion of individual segments of the limb.

It is desirable to minimize the restrictive nature of the instrumentation applied to the horse. For example, small, lightweight low-power devices are used, and wireless communication is used between the sensors and the hub. For example, the hub and each of the sensors includes a radio and a local (to the horse) wireless data network based on the Bluetooth standard can be used to communicate on one or more radio channels between the sensors and the hub. Other wireless approach can alternatively be used, for example, based on low-power ad-hoc data networks such as using the Zigbee or IEEE 802.15.4 standards), which may allow data to pass between the sensor and the hub in one or multiple hops (for example via other sensors acting as forwarding nodes). In some cases, wired connections may be preferable (such as USB, or Firewire), for example, if such a wire does not restrict motion, and the characteristics (such as bandwidth, power consumption, size, or weight) of the sensor are preferable if it does not require wireless connectivity.

Some devices may optionally function partially or completely without batteries relying only on parasitic energy from the motion of the horse, for example, using piezo-electric generators in horseshoes or electro-magnetic generators on a moving limb portion. In order to conserve power and extend battery life, some sensors can vary their transmission data rates based on their sensed signals, for example providing higher data rates when they measure more rapid changes. For example, an acceleration sensor on a hoof may transmit at a higher rate during a gallop than at a walk, and may transmit at different rates at different phases in each stride. The timing of and rate of data transmission may be determined by the sensor module, or by the hub, or by negotiation between them.

Communication between the hub 120 and the server 130 also uses a wireless data channel. For example, the hub can include an additional radio for communicating with the server, with the other radio being used to communicate with the sensors. A number of alternative types of radio channels can be used. For example, a dedicated point-to-point radio link may be used. A wireless data network can also be used, for example, based on a wireless Ethernet (such as 802.11a, 802.11b or 802.11g) standard. Using a wireless data network, multiple wireless access points can provide connectivity between the hub and the server over a relatively wide area, for example, from inside a stable to distant locations in a paddock or on a race course or a show jumping arena or a dressage ring or an eventing cross-country course. Wide area wireless communication can also be used, for example, based on cellular or satellite or wide area broadband wireless technology, such as GSM/GPRS or W-CDMA or CDMA1X or FLASH-OFDM or IEEE 802.16 or 802.20 data services. Using a wide area communication approach can provide global coverage for the monitoring, for example, allowing monitoring of a horse in transmit to a distant location, or during training or competing at that distant location.

Security of the data may be desirable for a number of reasons, including privacy of the data collected about a horse (that is preventing interception of or interference with the transmitted data) and authentication of the data that is to guarantee that the collected data was truly collected and not tampered with or altered in some way. One aspect of the system that provides security is encryption of the wireless link 125 that couples the hub 120 and the server 130. Similarly, wireless links 115 between the sensors 110 and the hub 120 are also optionally encrypted, although because of generally lower power and the limited nature of the data the threat of interception may be a less serious concern on these links. For authentication, data sent from the hub can be cryptographically signed to guarantee that the data was generated by the particular hub or by particular sensors on the horse.

Additional contextual data, such as date and time-of-day and position data may be included in the data sent to the server to time and location stamp the data and for use in further cryptographic authentication and/or verification of the data. For example, the hub can optionally include a GPS receiver that is used to determine the time and location data.

In addition to sensors such as accelerometers and strain or force or pressure sensors, which generally relate to collection of parameters that can be used to analyze the gait of a horse, the system can be used to collect and analyze other signals including physiological parameters and characteristics of the environment. For example, cardiovascular signals such as heart rate, blood oxygen level, and blood pressure can be collected and sent through the hub to the server. Similarly, audio or video measurements, such as recording of respiratory sounds (or air pressure) or endoscopic video can be collected. Also, signals related to the rider may be collected and used in conjunction with signals related to the horse. For example, signals that relate to the rider's position, stance, pressure on reigns, stirrups, or through their legs, or other activity can be collected, as can physiological signals such as the rider's heart rate or breathing rate.

In addition, sensor that measure environmental conditions, such as air temperature, humidity and pressure, can provide environmental data that can be collected and correlated with performance or physiological data. In particular, the signals can be associated with high speed or normal speed video monitoring of the horse.

The system can be used in a number of different applications. A first application relates to gait analysis. For example, sensors are temporarily attached to a horse and data collected for the purpose of evaluation or diagnosis, for example, for a duration of less than a day (such as a normal exercise regimen of approximately an hour). One type of analysis relates to detection of asymmetry in a horse's gait. For example, if motion or hoof pressure is asymmetrical (that is, from side to side), lameness may be indicated. In addition, pattern classification approaches, for example, based on statistical data collected from a population of other lame and sound horses, (or prior data collection for the same or another single horse) may be used for diagnosis.

Gait analysis can include a number of alternative types of processing of sensor signals, for example, depending on the sensor signal actually available and the information that is desired. The parameters that can be derived from sensor measurements include the height and length of the foot flight arc, stride length and rate, alterations in the foot flight, timing and distance of phases of the stride, the magnitude and timing of joint angles, extension of the limbs, range of motion, gluteal rise and fall, relative force and pressure on different hooves. The analysis can include related movements such as movement of the head up or down or from side to side to compensate for lameness, or motion alteration when moving in an arc in one direction or the other direction.

Part of the gait analysis can involve categorization of the gait in which the horse is moving, such as walk, trot, canter and gallop, or collected, working, medium and extended gaits. This categorization may be used on its own, or can be used in further data analysis, for example, to trigger analysis that is particular to a gait. For example, a certain type of detailed analysis may be applicable only at a trot, and the classification may be used to trigger the analysis. The analysis may be used to determine subtle lameness, as opposed to a binary classification of lame versus not lame.

Another part of gait analysis relates to measurement of signals related to the quality of motion of a horse's gait. The quality of motion includes characteristics which may depend on detailed aspects of limb motion, such as the trajectory of limb segments (such as "paddling," straight versus swaying from side to side, pointing and "flipping" of the hoof and so on), timing of various stages in the gait (such as dwell time, "hang time" immediately before the hoof hits the ground, and so on) and smoothness of the overall motion. Quantities characterizing the quality of motion of a horse's gait are derived from the underlying sensor signals, either in real time at the hub or on the server, or as part of a later analysis of sensor data.

Another application also relates to gait analysis, but the collection period may be longer than a day. For example, the sensors may be applied to the horse (including for example using instrumented horse shoes) and the data collected over a period of days, weeks, or longer. In such an approach, changes over time can be used to detect or predict conditions such as lameness. The extended period is not necessarily continuous. For example, the sensors may be applied to the horse during a regular training period each day. Alternatively, the sensors may be applied and kept on the horse continuously.

Another application involves a closed-loop diagnostic procedure. In this application, sensors are attached to the animal, and a first set of measurements and associated analysis are performed. Using a differential diagnosis or decision-tree approach (for example, based on expert knowledge or derived from empirical data), the results of the first analysis determine the next set of measurements to perform. It may be necessary to perform a different set of motions, or to reposition the sensors, or to use different sensors for each iteration. The diagnosis or decision process may be computer aided, for example, encoding the logic for which measurements to perform based on results of analysis in previous iterations.

One way of providing the data from the sensors to a user is with a graphical interface using tabular or graph representations of the data. The interface optionally permits a user to zoom in or drill down on particular displayed data to view more detailed information.

Extended monitoring, or repeated monitoring at time intervals (for example weekly) can also be used to identify trends. For example, data for a particular horse is stored at a server, and automated or computer-aided techniques are used to analyze the stored data. In one type of analysis, statistical deviation from past data is used to identify unusual events or trends, which could be associated with an injury. In another type of analysis, comparison is made between the data for one horse and data for another horse or for a population of horses.

In another application, the sensor data is used to track changes. One aspect of such tracking relates to tracking conditioning that is fitness and muscle strength of a horse based on quantitative parameters. For example, the system can provide information that is used to determine which muscle groups require additional emphasis in training. Another aspect of such tracking relates to rehabilitation or convalescence of a horse after an injury. For example, the quantitative data can be used to determine a best course of training during a recovery period after an injury.

A related application involves monitoring progress during recovery from an injury. Periodically (or even continuously) during care after an injury, the animal is monitored and characteristics, such as gait or performance characteristics, are recorded. These characteristics are then used to determine the recovery progress of the animal and/or to determine the type or amount of work the animal should perform. Progress can be measured by predetermined thresholds, and can be based on a comparison of previously monitored progress during recovery from previous injuries, for example, from a population of similar animals with similar injuries.

A related application involves evaluating or monitoring the training or the conditioning or the preparation of an animal. For example, data for the horse is used to determine what is the optimal training or conditioning regime. For example, this data is used to determine the effects of different approaches to shoeing of a horse, and to optimize the choice and fitting of shoes.

Another application relates to assessment of athletic performance or potential athletic performance of a horse. In such an application, rather that diagnosing an injury, physical parameters, for example, related to speed, endurance, jumping ability, and so on are collected using the system. This data may be used in combination with other objective measurements (for example conformation measurements or radiographs or physical examination) or subjective assessments. For example, objective and quantitative data about the physical, physiological and performance characteristics of top competitive horses can be used to provide an objective benchmark or target set of parameters, then over time the trends in the development of a cohort of horses towards these benchmark characteristics can be used to identify what the salient characteristics of younger or untrained horses are that correspond well with subsequent high levels of competitive performance when older or well-trained. For example, this information could then provide an objective basis for the assessment of potential purchases, and used to maximize the return on investment. This may apply to racehorses, as well as to showjumpers and other events.

A related application relates to assessment of the performance of people associated with the horse, and improving their performance. For example, this may involve providing a rider with quantitative feedback on how they are riding.

Another area relates to identification of a horse, for example, to prevent fraud in sale of the horse. Certain physical parameters, such as detailed gait patterns may be individual to a horse and not easy mimicked. Previously recorded and authenticated data for a particular horse can be used to determine later whether another horse is that same horse. For example, a statistical test can determine whether the new data for the horse is characteristic to that horse (for example, there is a low statistical probability that the data comes from a different horse), and discriminant analysis using data from other horses can identify derived features from the sensor measurements that provide high information related to the horse's identity.

Another fraud-related application is applicable to reduction of insurance fraud. For example, collection of quantitative data might be a condition of obtaining health-related insurance for a horse. An insurance underwriter could require that such collection of data span an extended continuous period, thereby making it difficult to hide certain conditions, for example, by using short acting medications.

Another application relates to safety, for example, during an equestrian event. Some events can be very dangerous for both the horse and the rider. In this application, relatively unobtrusive sensors are attached to the horse for the competition. The sensor data is monitored continuously during the event. Based on human monitoring or on an automated signal-processing algorithm, each horse in the event is tracked and if a high likelihood of injury is detected, the rider can be pulled from the course.

Other applications relate to long-term monitoring, for example, during the course of a pregnancy in which gynecological and/or fetal signals are monitored. In addition, monitoring can be targeted at the detection of colic in otherwise healthy animals.

The system also has application in situations in which the animal is confined, for example in a stall, in a vehicle while being transported or on a treadmill. In such an application, the hub is not necessarily attached to the horse and can be in a stationary location, possibly co-located or even hosted in the server (for example as a peripheral card or device in the server computer). Even though the animal is confined, the lack of wired connections between sensors on the horse and the rest of the system facilitates and simplifies the diagnostic or monitoring procedure.

In view of the wide variety of sensor types and algorithms that may be employed, in a preferred version of the system, a self-configuration feature enables parts of the system to be automatically configured based on the sensor data that is available.

One type of automatic configuration relates to automatic detection of the sensor data that is available. For example, various sensors may be attached to the horse and the hub automatically determines what data is available. The hub may also configure local processing algorithms, for example, to estimate gait features based on whatever sensor data is available. For example, if hoof pressure data is available, a different signal-processing algorithm may be employed than if only inertial data is available from limb extremities, and yet another algorithm may be employed when both pressure and inertial measurements are available.

The identification of the type of sensor, as the basis for auto-configuration of the system, can include the use of public standards, such as the IEEE 1451.4 standard for smart transducers that are very small or that are part of a distributed array.

The sensors may further identify themselves, for example, providing sensor parameters to the hub, which can be used to calibrate the data. Further, the system may automatically determine where on a horse the sensors are attached. For example, rather than having to identify which accelerometer sensor is attached on each leg of the horse, the system can automatically determine which signal is from which leg. Furthermore, link segment modeling may be used for analysis as well as automatic configuration. For example, based on a model of a horse's limbs, the particular limb segment to which each sensor is attached, as well as the location on that limb segment can be determined automatically. For example, the rider may indicate to the system that the horse is in a canter on a right lead, and a model of such a gait is then used to automatically calibrate the sensor locations. Sensor measurement parameters such as gains, offsets, rates or drift, and so on can also be automatically determined from measurements from the sensors.

Sensors can be of various types. For example, some sensors are "off-the-shelf" digital or analog devices using industry standard interfaces. For example, a USB-based or Bluetooth-based microphone or camera might be such a device. Alternatively, a sensor might use a common analog interface, and be connected directly to a compatible analog interface on a hub or sensor module. Other sensors are specialized devices, but can emulate standard devices. For example, an endoscope might have a USB interface that is the same as a standard USB video camera. Other devices may have non-standard interfaces, for example, using low-power radio networking communication. Finally, for some devices, the hub emulates a proprietary receiver, for example to receive heart-rate measurements.

Other types of automatic configuration may relate to automatic detection of the particular horse to which the sensors are attached. As an example, RFID technology can be used to identify the horse using a tag attached to the horse. As a related benefit of such technology, RFID data or related data can be used for authentication of the data.

The system may include automatic calibration of the sensors. For example, the data from a sensor may be used to calibrate for and compensate for gain, rates, offsets and drifts. Alternatively, the data from a number of sensors may be combined as the basis for this calibration, or this data from a particular horse and time and place may be combined with additional information from other trials or other horses.

Figure 2A:
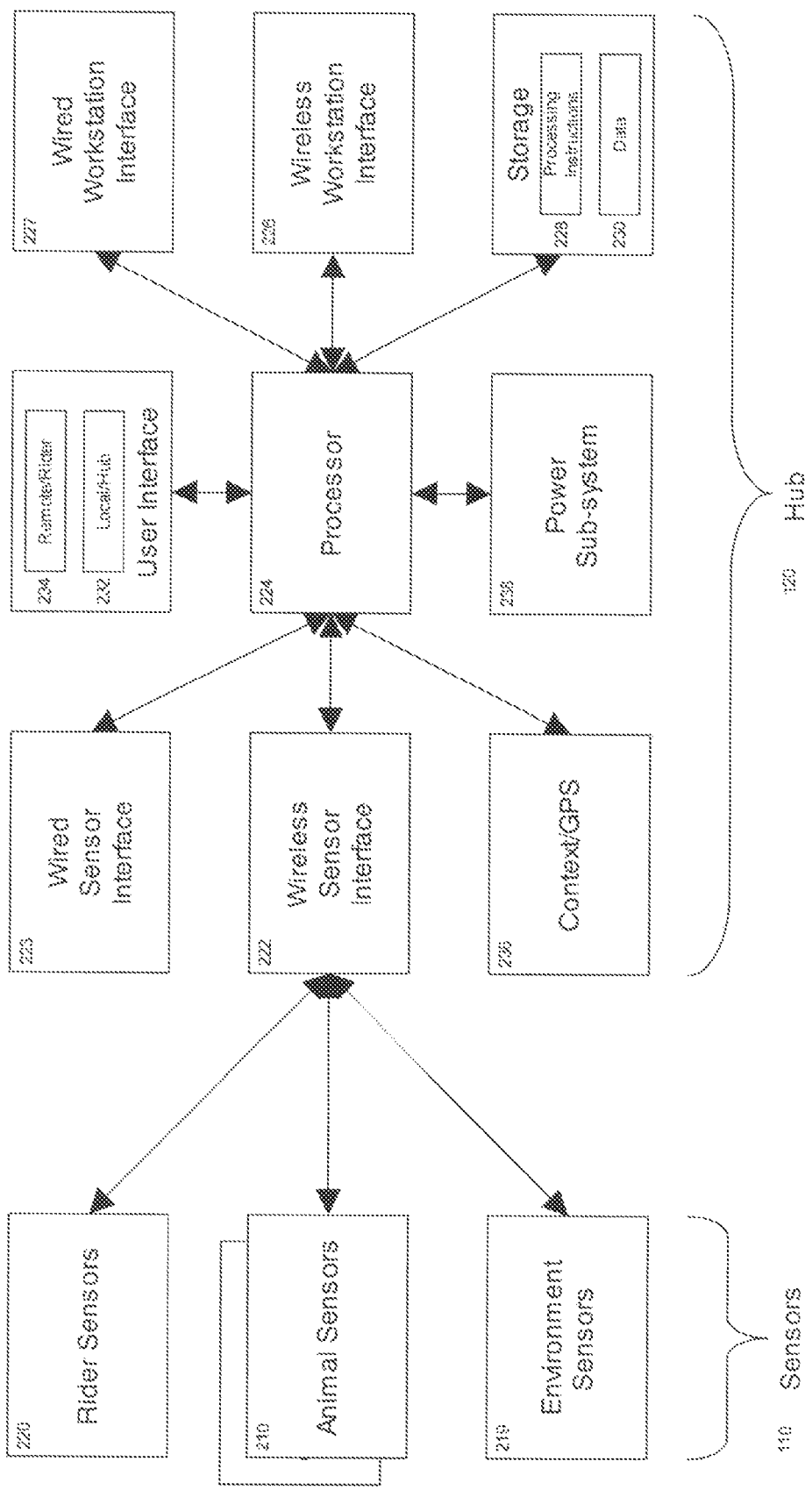
FIGS. 2A-B are block diagrams of the instrumentation, telemetry and informatics system.

Referring to FIG. 2A, an embodiment of the system includes sensors 110 and one or more hubs 120 that are local to the horse. The sensors 110 can include sensors for measuring characteristics of the animal ("animal sensors") 210, including gait-related sensors (such as accelerometers, pressure sensors, etc.), cardiovascular sensors, respiratory sensors, gastrointestinal sensors, and gynae/foetal sensors. Rider sensors 220 provide measurements related to the riders position, physiological state, etc. Environment sensors 219 provide measurements related to the temperature, humidity, etc. In addition, a context module 236, which can include a GPS receiver to determine the location of the horse and the recording time and can include a RFID reader to determine the identity of the horse (or the rider) can provide data to the hub 120.

The hub 120 includes a sensor communication interface 222 that provides a communication path to the sensors 110. A processor 224 is coupled to the sensor communication interface. The processor executes instructions (such as programs, procedures, scripts, and so on) that are stored in a processing instruction storage 230. The instructions can be permanently resident in the hub, for example in a read-only memory, loaded from a machine-readable medium, or downloaded over a communication link such as from a server 130. The hub also includes a data storage 228 that is used to hold sensor data, for example, as it is processed in the hub or as it is buffered for transmission to a server. A user interface 232 in the hub provides an interface to user display/controls 234. A server communication interface 226 provides a data communication path to a server 130.

Note that the hub is not necessarily attached to the horse, for example, on the saddle or in a weight pocket. In one alternative, the hub is carried by the rider. In another alternative, particularly when the horse is confined, the hub is in the proximity of the horse, for example, housed on a stall or in a trailer or near a pallet, rather than being carried by the horse. The hub can include special-purpose hardware, and can be hosted in a more generally available platform such as a personal digital assistant (PDA) or a cellular telephone (for example, acting as a data gateway to pass Bluetooth based sensor signals onto a GSM data network).

A hub 120 can be associated with a horse for an extended period, for example, being attached and removed from the horse as needed. At different times, it may communicate with different servers 130. Authentication techniques are used to prevent the hub from disclosing information to unauthorized servers, or to protect the data on a common server.

Figure 2B:
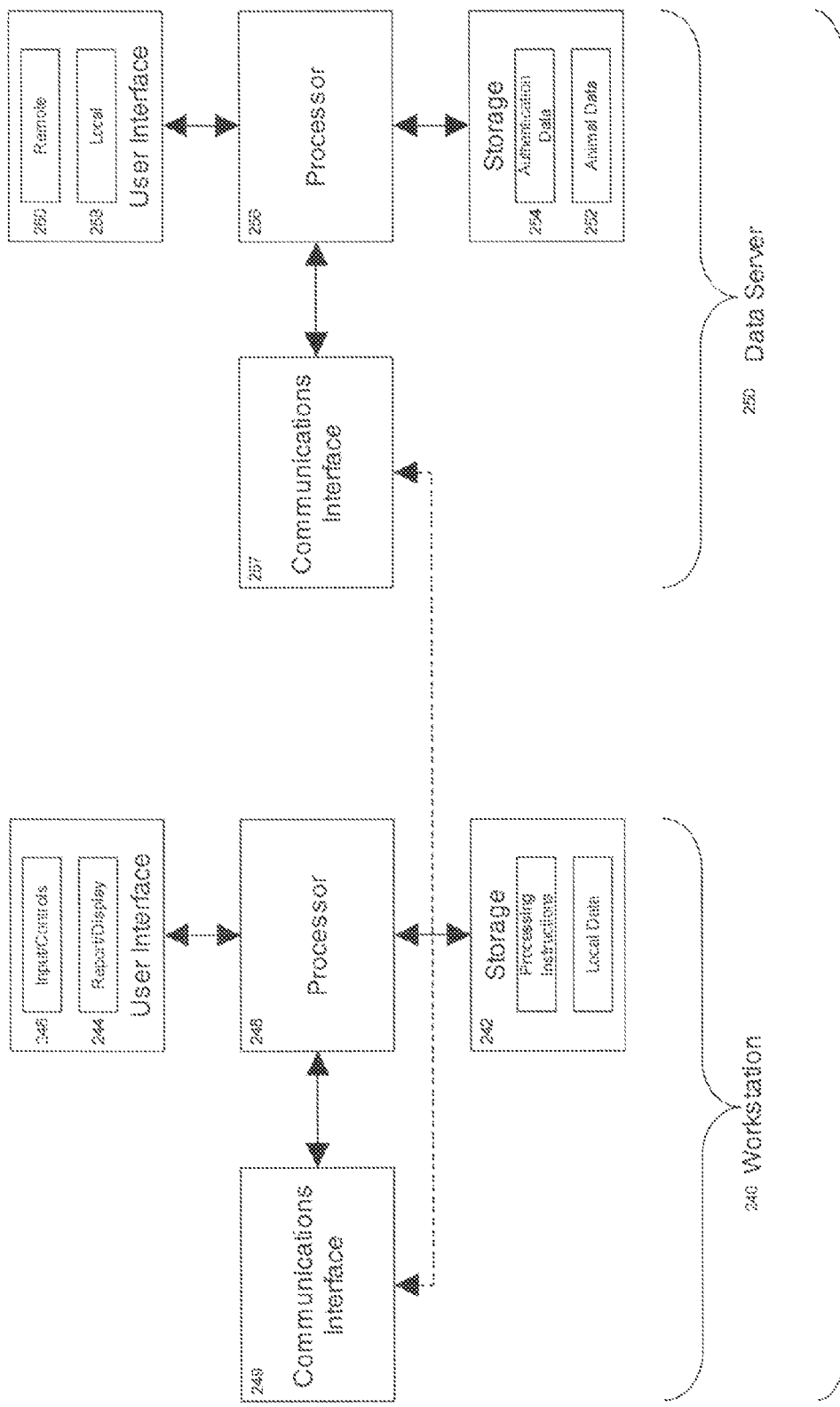

Referring to FIG. 2B, remote from the horse, a server 130 can include one or more workstations 240, each of which includes a data storage for data 242 and a user interface for report/display 244 and input/controls 246. Another computer can serve as a data server 250 and also includes a data storage 252. For example, the data server may be a centralized computer that serves as a secure repository for data that may be collected from different horses and at various venues each of which is served by a different workstation 240, or that may be retained for various purposes such as veterinary care or fraud prevention. The data server includes can include a secure data storage 252 with associated authentication data 254. The data server may include local user interfaces 258 and remote user interfaces 260 for viewing the data and controlling the system. The interfaces for displaying the data may be modular and configurable, capable of working from static pictures of a particular instant in time through faster than real-time, at different levels of aggregation and abstraction, from raw data through. Various types of graph or animation displays can be generated from the data. For example, sensor data or derived quantities can be displayed or visualized in graphical or numerical tabular form. Animations can also be generated from the data, for example, showing some or all of the animal in a schematic (for example, as a stick figure) or a realistic animation. Data from various sources can be synchronized and displayed together, for example, enabling synchronized display of actual video recordings of the animal and data derived from sensor measurements. Similar synchronization can be applied to other imaging techniques including MRI and ultrasound imaging.

In addition, remote monitoring and display of this information is possible, through wide area communication networks, such as the Internet, enabling tele-veterinary services, or an owner to monitor an exercise session, training regimen or competition.

This data may be associated with other data, such as structured or free-form notes, or other diagnostic images or measurements, provided by the rider, trainer or veterinarian.

Alternative versions of the system are applicable to different animals than horses. Some of the techniques are particularly related to gait analysis of quadrupeds, but in general, the approaches are not limited in this way. Indeed, some applications of the system are applicable to monitoring of humans, for example, during athletic events.

A number of alternative system architectures are possible within the general approach described above. Alternative communication technologies are discussed above. In addition, the arrangement of the modules can be different. For example, a hub may not be used if the sensors can communicate directly to the server. In such a case, all the processing of the data occurs at the server. In another alternative, all the processing occurs in real time at the hub and the server is not needed for real-time processing. For example, the server may provide a repository for data that is recorded on the hub and periodically transferred to the server.

Various different types of authentication and related techniques can be used in the system. These include approaches for maintaining privacy of data, ensuring that data has not been tampered with, and providing third party verification regarding the time and place of collection and possibly the identify of the animal that generated the data.

Authentication can be based on a chain of trust, for example, based on a chain of cryptographic certificates used to sign data. For example, data can be certified as having been collected through a particular hub, and the hub can be certified as having been associated with a particular horse by an entity (or chain of entities) that are trusted. Further authentication can be based on continuity of measurement and continuity of characteristic features of motion, so that once a hub is associated with an animal, there can be some level of certainty that measurements from that hub remain from the same animal.

The hub can be implemented using a programmable processor and under the control of software that is stored on a medium such as a magnetic disk or solid-state memory in the hub. The programmable processor can be a special-purpose processor or can be a general-purpose processor. The hub can use a standard operating system (such as Linux). The software for the hub can be distributed on media such as optical disks, or can be distributed over a data network (i.e., as a propagated signal) and downloaded into the hub. The server computers can also be controlled by software that is executed on a programmable processor, with the software being stored on a medium, which would typically include a magnetic disk.

It is to be understood that the foregoing description is intended to illustrate and not to limit the scope of the invention, which is defined by the scope of the appended claims. Other embodiments are within the scope of the following claims.

What is claimed is:

1. A method for determining potential performance of an animal comprising:
   acquiring objective measurements from the animal, including acquiring sensor measurements sufficient for determining a quality of motion that depends at least in part on a trajectory of a limb of the animal;
   acquiring measurements from other animals and storing performance attributes of the other animals;
   comparing the objective measurements with criteria derived from the measurements acquired from the other animals; and
   predicting potential performance based on a result of the comparison;
   wherein acquiring the measurements from the other animals includes acquiring measurements from the other animals at a stage of development corresponding to that of the animal for which potential performance is to be determined, and storing the performance attributes of the other animals includes storing attributes of the other animals corresponding to a later stage of development.

2. The method of claim 1 further comprising processing the acquired objective measurements, including deriving motion-related parameters from objective measurements.

3. The method of claim 2 wherein said motion-related parameters include a parameter from the group consisting of: stride length; stride rate; height and length of a foot flight arc; alterations in foot flight; magnitude and timing of joint angles; extension of a limb; range of limb motion; and relative force and pressure on different hooves.

4. The method of claim 2 wherein said processing the acquired objective measurements further includes determining the quality of motion that depends at least in part on a trajectory of a limb of the animal.

5. The method of claim 4 wherein said quality of motion includes a characteristic that depends on a degree of a defined type of motion.

6. The method of claim 4 wherein said quality of motion depends on trajectories of multiple limb segments.

7. The method of claim 6 wherein said quality of motion depends on relative motion of said limb segments.

8. A method for determining potential performance of an animal comprising:
   acquiring objective measurements from the animal, including acquiring sensor measurements sufficient for determining a quality of motion that depends at least in part on a trajectory of a limb of the animal;

comparing the objective measurements with criteria derived from measurements acquired from other animals;

predicting potential performance based on a result of the comparison; and processing the acquired objective measurements, including deriving motion-related parameters from objective measurements;

wherein said processing the acquired objective measurements further includes determining the quality of motion that depends at least in part on a trajectory of a limb of the animal;

wherein said quality of motion includes a characteristic that depends on a degree of a defined type of motion; and wherein the defined type of motion includes paddling.

9. A method for determining potential performance of an animal comprising:

acquiring objective measurements from the animal, including acquiring sensor measurements sufficient for determining a quality of motion that depends at least in part on a trajectory of a limb of the animal;

comparing the objective measurements with criteria derived from measurements acquired from other animals;

predicting potential performance based on a result of the comparison; and processing the acquired objective measurements, including deriving motion-related parameters from objective measurements;

wherein said processing the acquired objective measurements further includes determining the quality of motion that depends at least in part on a trajectory of a limb of the animal;

wherein said quality of motion includes a characteristic that depends on a degree of a defined type of motion; and wherein the defined type of motion includes at least one of pointing and flipping of a hoof.

10. A method for determining potential performance of an animal comprising:

acquiring objective measurements from the animal, including acquiring sensor measurements sufficient for determining a quality of motion that depends at least in part on a trajectory of a limb of the animal;

comparing the objective measurements with criteria derived from measurements acquired from other animals;

predicting potential performance based on a result of the comparison; and processing the acquired objective measurements, including deriving motion-related parameters from objective measurements;

wherein said processing the acquired objective measurements further includes determining the quality of motion that depends at least in part on a trajectory of a limb of the animal;

wherein said quality of motion includes a characteristic that depends on a degree of a defined type of motion; and wherein the defined type of motion includes smoothness of overall limb motion.

* * * * *